US010663539B2

(12) United States Patent
Soejima et al.

(10) Patent No.: US 10,663,539 B2
(45) Date of Patent: May 26, 2020

(54) MAGNETIC RESONANCE IMAGING APPARATUS AND METHOD OF INSTALLING MAGNETIC RESONANCE IMAGING APPARATUS

(71) Applicant: Toshiba Medical Systems Corporation, Otawara-shi (JP)

(72) Inventors: Kazuyuki Soejima, Otawara (JP); Naoki Imamura, Nasushiobara (JP); Naho Imamura, Nasushiobara (JP)

(73) Assignee: Canon Medical Systems Corporation, Otawara-shi (JP)

(*) Notice: Subject to any disclaimer, the term of this patent is extended or adjusted under 35 U.S.C. 154(b) by 226 days.

(21) Appl. No.: 15/631,281

(22) Filed: Jun. 23, 2017

(65) Prior Publication Data
US 2017/0293002 A1 Oct. 12, 2017

Related U.S. Application Data

(63) Continuation of application No. PCT/JP2015/086088, filed on Dec. 24, 2015.

(30) Foreign Application Priority Data

Dec. 24, 2014 (JP) .................. 2014-261034

(51) Int. Cl.
*G01R 33/34* (2006.01)
*G01R 33/38* (2006.01)
(Continued)

(52) U.S. Cl.
CPC ....... *G01R 33/34007* (2013.01); *G01R 33/30* (2013.01); *G01R 33/3614* (2013.01);
(Continued)

(58) Field of Classification Search
CPC .......... G01R 33/34007; G01R 33/3802; G01R 33/543; G01R 33/3614; G01R 33/30; G01R 33/36; G01R 33/422; A61B 5/0555
(Continued)

(56) References Cited

U.S. PATENT DOCUMENTS 7,221,159 B2 * 5/2007 Griffiths ............... G01R 33/283
324/318
2003/0058502 A1 * 3/2003 Griffiths ............... G01R 33/283
398/139

(Continued)

FOREIGN PATENT DOCUMENTS

JP 54-20505 2/1979
JP 63-272329 11/1988
(Continued)

OTHER PUBLICATIONS

International Search Report dated Mar. 29, 2016 in PCT/JP2015/086088 filed Dec. 24, 2015 (with English Translation).
(Continued)

Primary Examiner — Susan S Lee
(74) Attorney, Agent, or Firm — Oblon, McClelland, Maier & Neustadt, L.L.P.

(57) ABSTRACT

According to one embodiment, a magnetic resonance imaging apparatus installed in a shield room comprises a gantry, a table, and at least one unit. The gantry includes a static magnetic field magnet, a gradient magnetic field coil, and an RF coil. The subject is to be placed on the table. The at least one unit relates to control of the magnetic resonance imaging apparatus and is configured to include at least one opening on a upper surface on for maintenance and inspection.

17 Claims, 11 Drawing Sheets

(51) Int. Cl.
*G01R 33/30* (2006.01)
*G01R 33/36* (2006.01)
*G01R 33/54* (2006.01)
*G01R 33/422* (2006.01)
*A61B 5/055* (2006.01)

(52) U.S. Cl.
CPC ....... *G01R 33/3802* (2013.01); *G01R 33/543* (2013.01); *A61B 5/0555* (2013.01); *G01R 33/36* (2013.01); *G01R 33/422* (2013.01)

(58) Field of Classification Search
USPC .......... 324/300–322; 600/407–435; 381/128–131
See application file for complete search history.

(56) References Cited

U.S. PATENT DOCUMENTS

2006/0197530 A1  9/2006  Damadian et al.
2014/0097844 A1*  4/2014  Tomiha .............. G01R 33/3692
                                    324/321
2017/0293002 A1* 10/2017  Soejima ................ G01R 33/30

FOREIGN PATENT DOCUMENTS

| JP | 1-308536 | 12/1989 |
| JP | 11-74672 | 3/1999 |
| JP | 2001-323550 | 11/2001 |
| JP | 2002-143123 | 5/2002 |
| JP | 2007-167433 | 7/2007 |
| JP | 2008-514299 | 5/2008 |
| WO | WO 2013/153801 A1 | 10/2013 |

OTHER PUBLICATIONS

Written Opinion dated Mar. 29, 2016 in PCT/JP2015/086088 filed Dec. 24, 2015.

* cited by examiner

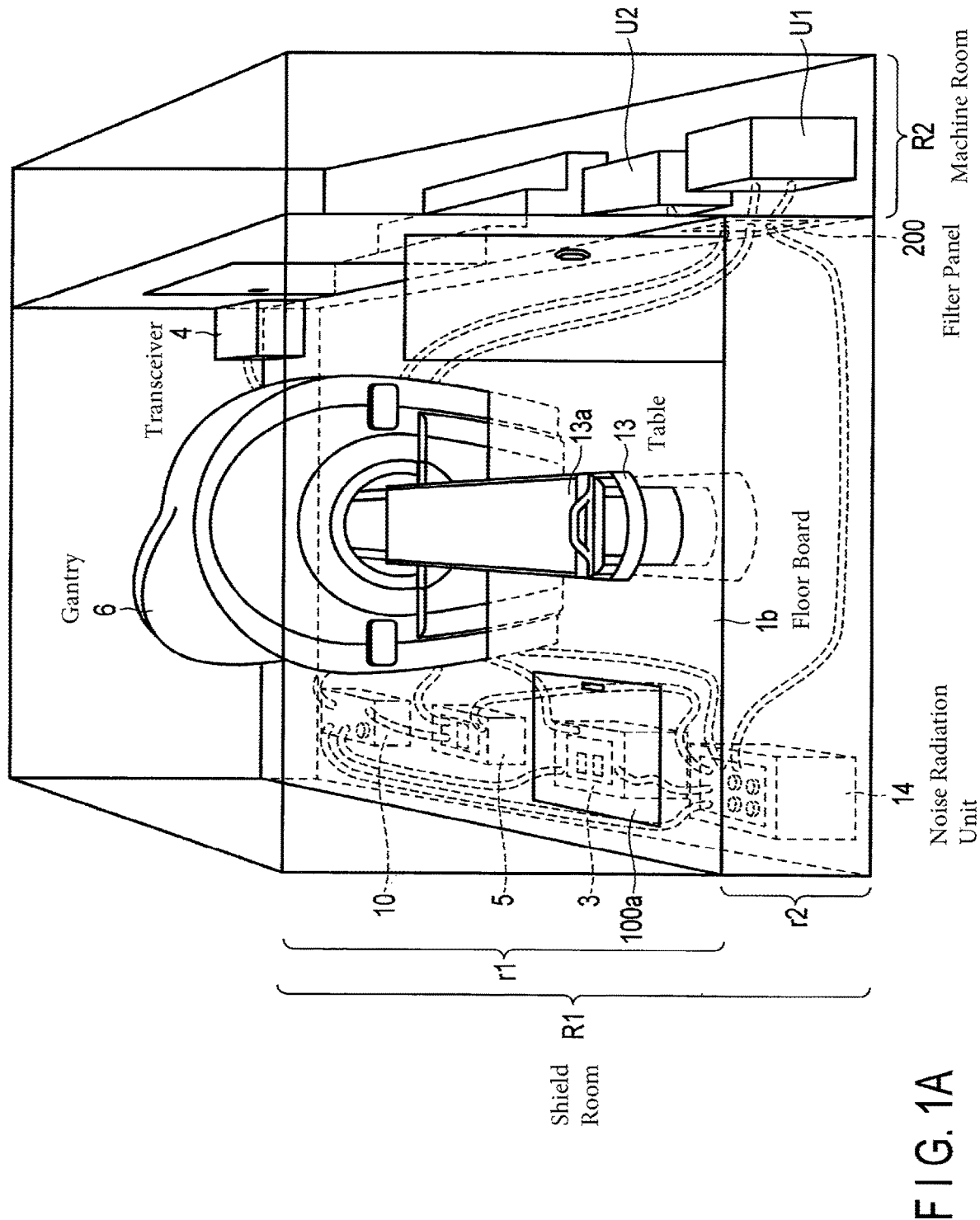
F I G. 1A

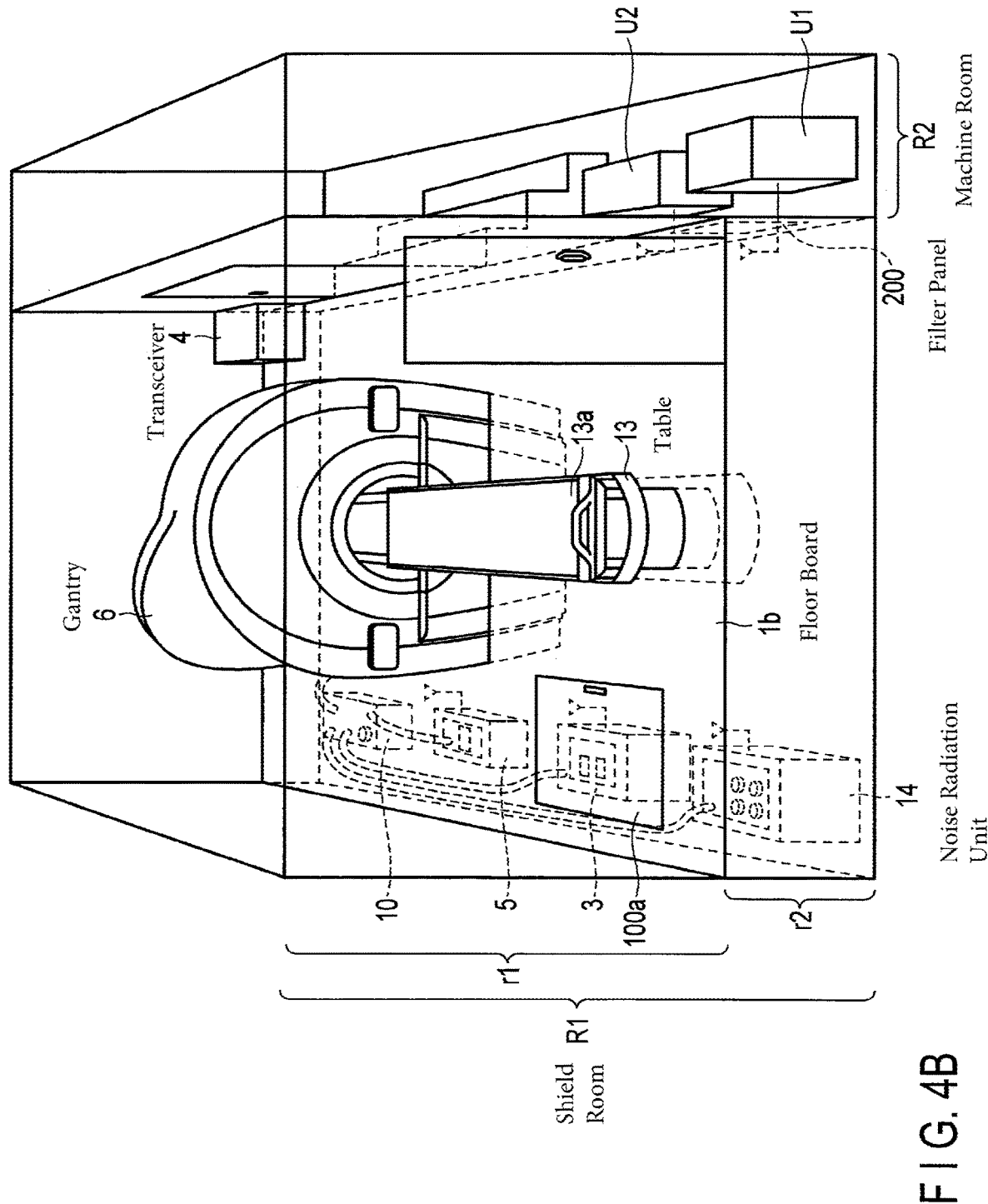
F I G. 4B

MAGNETIC RESONANCE IMAGING APPARATUS AND METHOD OF INSTALLING MAGNETIC RESONANCE IMAGING APPARATUS

CROSS-REFERENCE TO RELATED APPLICATIONS

This application is a Continuation Application of PCT Application No. PCT/JP2015/086088, filed Dec. 24, 2015 and based upon and claiming the benefit of priority from the Japanese Patent Application No. 2014-261034, filed Dec. 24, 2014, the entire contents of all of which are incorporated herein by reference.

FIELD

Embodiments described herein relate to a magnetic resonance imaging apparatus and a method of installing the magnetic resonance imaging apparatus.

BACKGROUND

An MRI (Magnetic Resonance Imaging) apparatus is widespread in the field of medical image diagnosis. MRI is an imaging method based on a magnetic resonance phenomenon. This imaging method magnetically excites, using an RF (Radio Frequency) signal of a Larmor frequency, the spins of atomic nuclei (for example, $^1H$) in a subject placed in a space in which a static magnetic field is formed and reconstructs an image from an NMR (Nuclear Magnetic Resonance) signal generated by the excitation.

Normally, various units including a host computer, power supply units, and the like are installed in a room called a machine room that is different from an imaging room. This is due to the prevention of noise radiation from the various units and the prevention of influence on the static magnetic field formed in the imaging room.

On the other hand, in recent years, there is a tendency to install the various units not in the machine room but in the imaging room in order to realize a space saving installation.

However, in this case, it is necessary to make the various units resistant to the magnetic field and suppression of the noise radiation, and problems such as cost increase are assumed.

BRIEF DESCRIPTION OF THE DRAWINGS

FIG. 1A is a bird's-eye view showing a magnetic resonance imaging apparatus according to the first embodiment and a shield room in which the magnetic resonance imaging apparatus is installed;

FIG. 4B is a bird's-eye view showing a magnetic resonance imaging apparatus according to the first modification and a shield room in which the magnetic resonance imaging apparatus is installed;

DETAILED DESCRIPTION

Figure 1B:
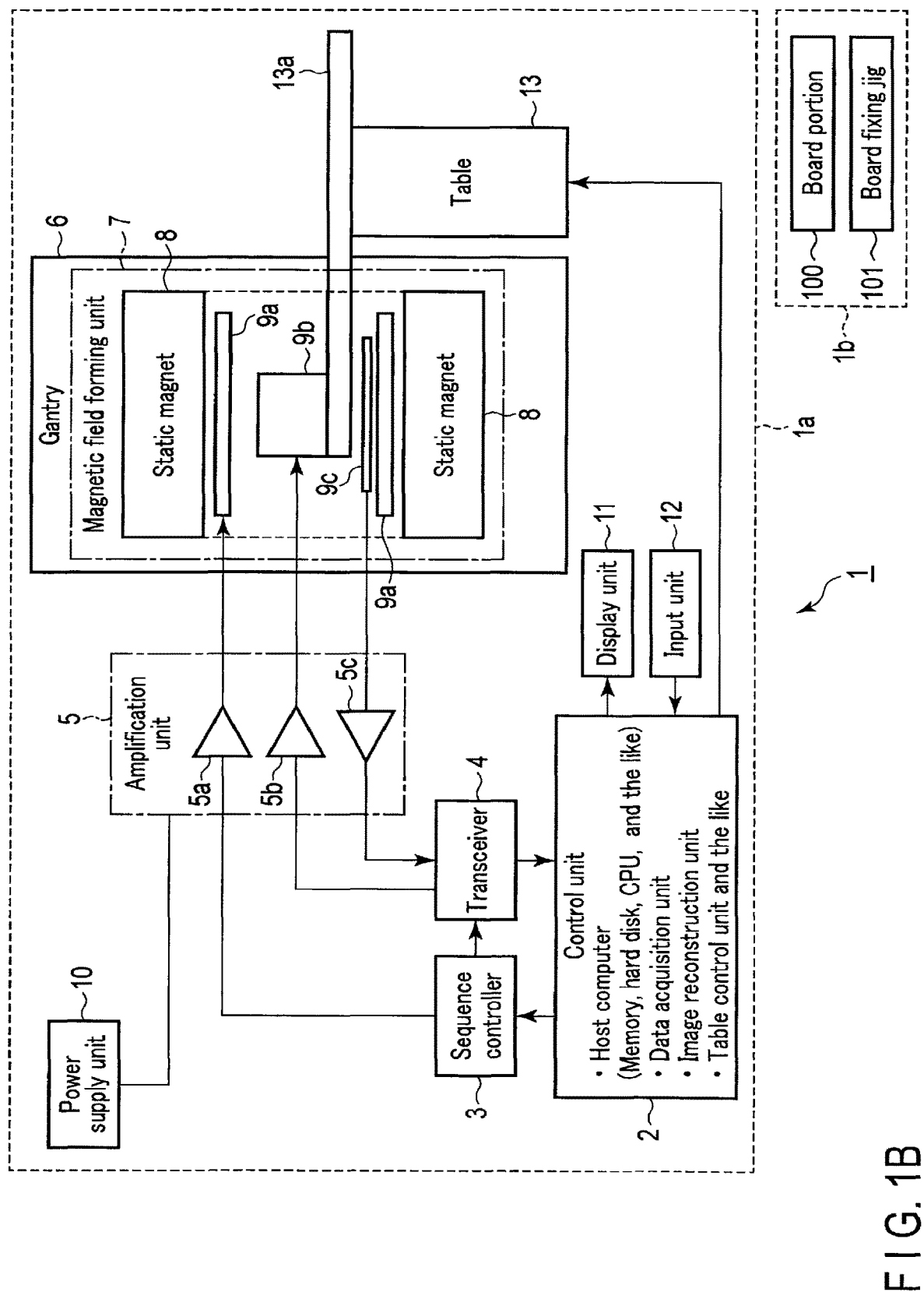
FIG. 1B is a block diagram showing an example of a magnetic resonance imaging system according to the first embodiment comprising a magnetic resonance imaging apparatus.

According to one embodiment, a magnetic resonance imaging apparatus installed in a shield room comprises a gantry, a table, and at least one unit. The gantry includes a static magnetic field magnet, a gradient magnetic field coil, and an RF coil. The subject is to be placed on the table. The at least one unit relates to control of the magnetic resonance imaging apparatus and is configured to include at least one opening on a upper surface on for maintenance and inspection.

Preferred embodiments will now be described with reference to the accompanying drawing. Note that in the following explanation, the same reference numerals denote constituent elements having almost the same arrangements, and a repetitive explanation will be made only when necessary.

(First Embodiment)

FIG. 1A is a bird's-eye view showing a magnetic resonance imaging apparatus 1a according to the first embodiment and a shield room R1 and the like in which the magnetic resonance imaging apparatus is installed. FIG. 1B is a block diagram showing an example of a magnetic resonance imaging system 1 according to the first embodiment comprising the magnetic resonance imaging apparatus 1a and the floor board 1b.

As shown in FIG. 1A, a floor board 1b is laid at a predetermined height from the floor surface of the shield room R1. The space surrounded by the floor board 1b, the ceiling of the shield room R1, and the side wall of the shield room (i.e., the space above the floor board 1b) forms the imaging room r1. On the other hand, the space surrounded by the floor board 1b, the floor surface of the shield room R1, and the side wall of the shield room (i.e., the space below the floor board 1b) forms the storage room r2. Magnetic shielding processing and high-frequency noise shielding (or blocking) processing are applied to the floor board 1b. Therefore, the imaging room r1 and the storage room r2 are electromagnetically shielded each other.

The magnetic resonance imaging apparatus 1a comprises a control unit 2, a sequence controller 3, a transceiver 4, an amplification unit 5, a gantry 6, a power supply unit 10, a display unit 11, an input unit 12, and a table 13. First, the structure and the function of each unit will be described.

The control unit 2 controls the overall operation of the magnetic resonance imaging apparatus 1a. The control unit 2 includes, for example, a host computer including a memory, a hard disk, a CPU, and the like, a data acquisition unit that acquires data (an electrical signal based on an NMR signal) transmitted from the transceiver, an image reconstruction unit, such as an image processor, that reconstructs an MR image from the acquired data, and a table control unit, such as a motor driving control processor, that adjustably controls the table 13. However, the structure and the function are not limited to this. Note that details of the operation will be described later in association with an explanation of the remaining portions.

The sequence controller 3 is connected to the transceiver 4 and a gradient driver 5a of the amplification unit 5. The sequence controller 3 controls sequences concerning transmission of an electrical signal used to generate a gradient magnetic field and transmission/reception (via the transceiver 4) of an electrical signal used to generate an RF (properly speaking, a magnetic field component of an RF) pulse. That is, the sequence controller 3 transmits a trigger to a connection destination at a predetermined timing.

The transceiver 4 transmits, via a transmitter 5b, an electrical signal used to generate an RF pulse for exciting atomic nuclei in a subject. In addition, the transceiver 4 receives, via a preamplifier 5c, an electrical signal based on an NMR signal generated when the atomic nuclei excited by the RF pulse return to the ground state. The transceiver 4 also transmits the electrical signal based on the NMR signal to the control unit 2.

The amplification unit 5 is a general term for the gradient driver 5a (an amplifier that amplifies and transmits an electrical signal used to generate a gradient magnetic field), the transmitter 5b (an amplifier that amplifies and transmits an electrical signal used to generate an RF pulse), and the preamplifier 5c (an amplifier that amplifies and transmits an electrical signal based on an NMR signal). The gradient driver 5a transmits the electrical signal to a gradient field coil 9a in synchronism with a trigger from the sequence controller such that the gradient field coil 9a forms a gradient magnetic field. The transmitter 5b transmits the electrical signal to an RF transmission coil 9b in synchronism with a trigger from the transceiver 4. The preamplifier 5c amplifies the electrical signal (weak) based on the NMR signal obtained from the subject via an RF reception coil 9c and transmits the electrical signal to the transceiver 4.

The gantry 6 includes a static field magnet 8, the gradient field coil 9a, the RF transmission coil 9b, and the RF reception coil 9c. The static field magnet 8, the gradient field coil 9a, the RF transmission coil 9b, and the RF reception coil 9c will generically be referred to as a magnetic field forming unit 7.

In this embodiment, the static field magnet 8 is assumed to be a general superconducting magnet. The static field magnet 8 forms a static magnetic field in the space in which the subject is placed. Note that the static field magnet 8 can be either a resistive magnet or a permanent magnet.

The gradient field coil 9a forms a gradient magnetic field in response to input of the electrical signal from the gradient driver 5a. Note that the gradient field coil 9a includes three coils corresponding to three, x-, y-, and z-axes. In FIG. 1B, only one gradient field coil 9a is defined to prevent complication of the drawing. By applying the gradient magnetic field to the static magnetic field, each atomic nucleus in the subject attains a Larmor frequency that changes depending on the position of the atomic nucleus. In other words, it is possible to discriminate the position information of a section from the NMR signal based on the difference in the Larmor frequency.

The RF transmission coil 9b transmits the RF pulse to the subject in response to the input of the electrical signal from the transmitter 5b. The RF pulse excites atomic nuclei in the subject which correspond to a unique Larmor frequency.

The RF reception coil 9c receives the NMR signal generated when the atomic nuclei in the subject return from the excited state to the ground state, and transmits an electrical signal (weak) based on the NMR signal to the preamplifier 5c.

Note that in this embodiment, the RF transmission coil 9b and the RF reception coil 9c are separate coils. However, a single coil may be used as the RF transmission coil 9b and the RF reception coil 9c.

The power supply unit 10 includes a plurality of power supplies, for example, five power supplies, and applies voltages to the amplifiers (corresponding to the gradient field coil 9a including three coils, the RF transmission coil 9b, and the RF reception coil 9c, respectively) in the amplification unit.

The display unit 11 is connected to the control unit 2 and, for example, displays an obtained MRI image.

The input unit 12 is connected to the control unit 2 and, for example, accepts an instruction input from an operator such as a doctor via a switch button, a mouse, a keyboard, or the like. The instruction input is transferred to the host computer in the control unit 2. The host computer executes predetermined control and calculation in accordance with the instruction input. For example, assume a case in which the operator wants to focus only a predetermined ROI (Region Of Interest) in an MRI image displayed on the display unit 11 and enlarge that portion. The input unit 12 accepts an instruction input concerning enlargement of the ROI by the operator. The instruction input is transferred to the host computer. The host computer executes enlargement processing of the MRI image. The display unit 11 displays the MRI image that has undergone the enlargement processing.

The table 13 is installed on the floor surface of the shield room R1 and includes an adjustment mechanism (not shown) capable of adjusting the position in the longitudinal direction of the tabletop 13a. The table control unit in the control unit 2 moves the tabletop 13a in the longitudinal direction via the adjustment mechanism to arrange the subject placed on the tabletop 13a in a subject arrangement space located inside the gantry 6.

The table 13 of the magnetic resonance imaging apparatus 1a shown in FIG. 1A does not include a mechanism for height adjustment of the tabletop 13a. This is due to the following reason. That is, the floor surface of the imaging room r1 shown in FIG. 1A, namely the floor board 1b is installed at a predetermined height from the floor surface of the shield room R1. The tabletop 13a of the table 13 is located at the height of the bore of the gantry 6 without vertically moving, and is at such a height that the subject on the floor board 1b can easily go up and down. Therefore, it is not necessary to provide a vertical movement mechanism of the tabletop 13a on the table 13.

In general, the upward and downward movements of the tabletop 13a may give fear to a child. Also, for an elderly person, it may be physically difficult for the person to go up and down to the tabletop 13a. According to the magnetic resonance imaging apparatus 1a shown in FIG. 1A, it is unnecessary to move the tabletop 13a up and down when the subject is going up and down onto the tabletop 13a or the tabletop 13a is inserted into the bore of the gantry 6. Therefore, it is possible to perform imaging safely without giving a physical load to the subject or a psychological burden. Further, since it is unnecessary to move the tabletop 13a up and down, it is possible to save the power corresponding to that.

Figure 1C:
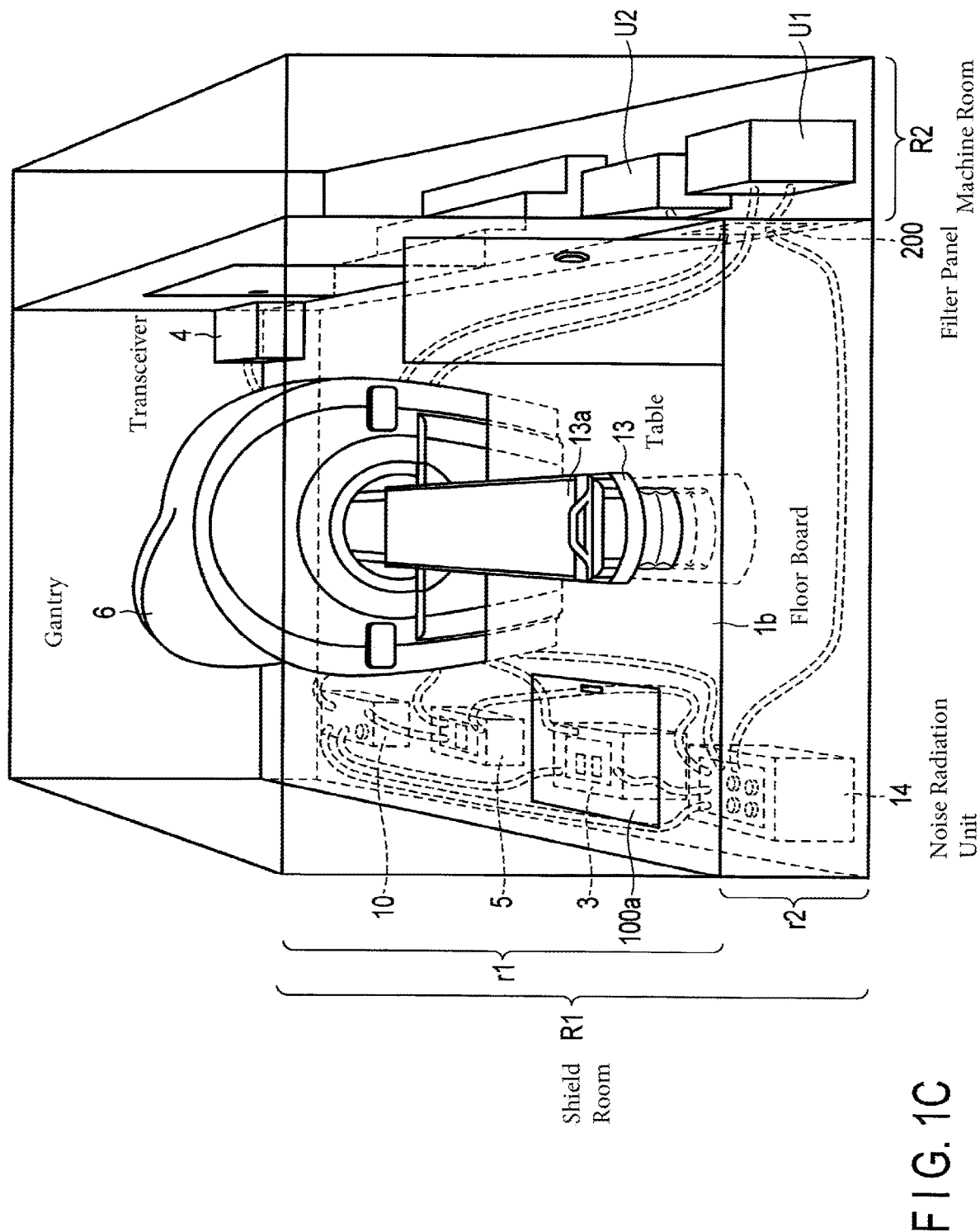
FIG. 1C is a bird's-eye review showing a magnetic resonance imaging apparatus according to the first modification and a shield room in which the magnetic resonance imaging apparatus is installed.

Note that without being restricted to the example shown in FIG. 1A, the table 13 having the height adjusting mechanism of the tabletop 13a, as shown in FIG. 1C, may be installed on the floor surface of the shield room R1 as necessary.

The floor board 1b forms a floor of the imaging room r1 and includes a board portion 100 (for example, a nonmetal plate made of a resin or the like) that has undergone magnetic shielding processing and high-frequency noise insulation (or blocking) processing, and a board fixing jig 101 (fixing means).

The board fixing jig 101 is a jig that fixes the board portion 100 to the magnetic resonance imaging apparatus 1a. This jig includes, for example, concave/convex portions, screw holes, and the like. The magnetic resonance imaging system 1 according to the embodiment is implemented by combining the magnetic resonance imaging apparatus 1a and the floor board 1b.

From the viewpoint of securing the strength, in addition to the board fixing jig 101, a support or a beam may be used to support the board portion 100. In addition, the board portion 100 does not have to be an integral structure, but may be realized by assembling a plurality of panels.

Next, how the magnetic resonance imaging apparatus 1a is installed in the imaging room r1 and the storage room r2 will be described.

Figure 2:
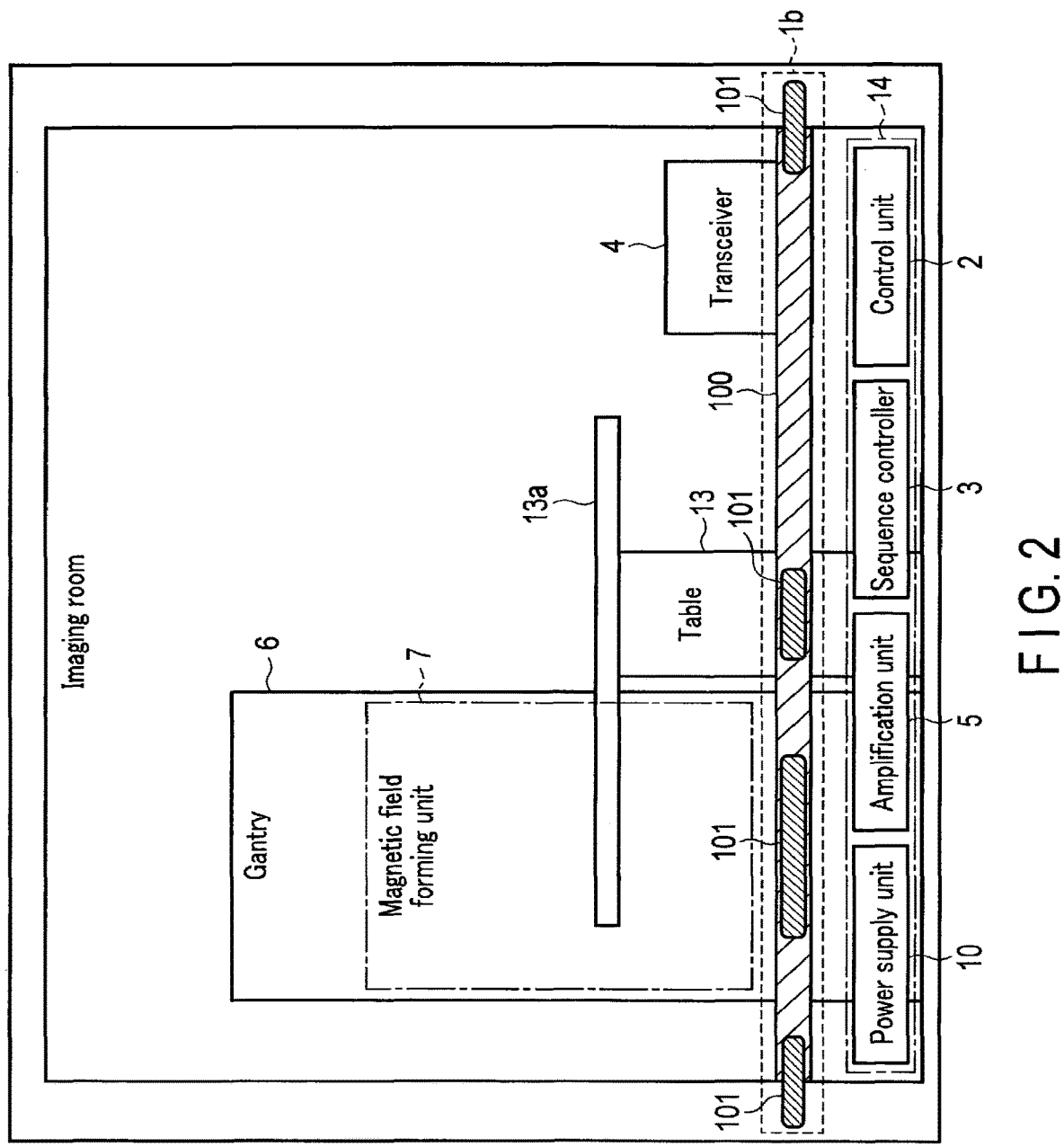
FIG. 2 is a plan view showing an example of a magnetic resonance imaging system according to the first embodiment comprising the magnetic resonance imaging apparatus.

FIG. 2 is a plan view showing an example of an installation form of the magnetic resonance imaging apparatus 1a according to the first embodiment.

In the example shown in FIG. 2, the gantry 6, the table 13, the control unit 2, the sequence controller 3, the amplification unit 5, and the power supply unit 10 are placed on the surface of the shield room R1 (that is, in the storage room r2). Hereinafter, the control unit 2, the sequence controller 3, the amplification unit 5, and the power supply unit 10 will be referred to as a noise radiation unit 14 because these units may generate high-frequency noise that interferes with the frequency band of the RF. The board portion 100 in the floor board 1b is fixed to the magnetic resonance imaging apparatus 1a (for example, the gantry 6 and the table 13 in FIG. 2) and the wall surface of the shield room R1 via the board fixing jig 101. On the other hand, the transceiver 4 is placed on the upper surface of the floor board 1b (that is, in the imaging room r1).

The gantry 6 and the table 13 are installed on the floor of the shield room R1, penetrate the floor board 1b, and are located across both the storage room r2 and the imaging room r1. Hence, the floor board 1b is formed in advance or during installation in accordance with the shape of the gantry 6 and the shape of the table 13 penetrating the floor board, and the shape of the wall surface of the shield room R1 (the shape of the horizontal section of the shielding room R1).

The board portion 100 of the floor board 1b undergoes magnetic shielding processing and high-frequency noise insulation processing, as described above. That is, the board portion 100 includes a magnetic shielding layer and a high-frequency prevention (RF prevention) layer. The magnetic field forming unit 7 generates a magnetic field (a static magnetic field generated by the static field magnet 8 and a gradient magnetic field generated by the gradient field coil 9a) for magnetic resonance imaging. The magnetic shielding layer of the board portion 100 shields the magnetic field so as to realize the magnetic field space in the imaging room r1 and not in the storage room r2.

On the other hand, the noise radiation unit 14 often radiates high-frequency noise (RF noise) close in frequency to the RF used for magnetic resonance imaging during its operation. This can occur either when the various units in the noise radiation unit 14 are connected by cables or when wireless communication is performed. The high-frequency prevention layer of the board portion 100 shields the high-frequency noise, thereby preventing propagation of the high-frequency noise to the first space.

The floor board 1b also functions as a floor of the imaging room r1. Therefore, the doctor and the subject can freely move on the floor board 1b.

In the magnetic resonance imaging apparatus 1a according to the first embodiment shown in FIG. 1A or the like, the gantry 6 is installed on the floor surface of the shield room R1. Therefore, leakage of the magnetic field from the gap between the gantry 6 and the floor board 1b to the storage room r2 and leakage of the high-frequency noise by the noise radiation unit 14 to the imaging chamber r1 exist. However, the leakage is weak as compared to a case in which the floor board 1b is not installed. To prevent the weak leakage, the magnetic shielding properties and high-frequency prevention properties of the gantry 6 may be enhanced.

In the examples shown in FIGS. 1A and 1C, a machine room R2 adjacent to the shield room R1 is provided. In the machine room R2, a desired device or machine among the control unit 2, the sequence controller 3, the amplification unit 5, the power supply unit 10, and other units of the magnetic resonance imaging apparatus 1a can be installed as needed (FIGS. 1A and 1C illustrate formal units U1 and U2 as the control unit 2, the sequence controller 3, or the like). However, installation of the machine room R2 is not indispensable. For example, by placing the units U1 and U2 provided in the machine room R2 into the storage room r2, the machine room R2 can be reduced or omitted, thereby realizing further space saving.

(Wiring)

In the magnetic resonance imaging apparatus 1a according to the present embodiment, the noise radiation unit 14 is installed in the storage room r2, and the magnetic field formation unit 7, the tabletop 13a, etc. are installed in the imaging room r1. Further, as required, a predetermined unit U1 or the like of the magnetic resonance imaging apparatus 1a can be installed in the machine room R2. Thus, it is necessary to be realized the cable wiring between the units arranged in different spaces while maintaining the electromagnetic shielding properties of the shield room R1 and the imaging room r1.

Therefore, in the magnetic resonance imaging apparatus 1a according to the present embodiment, a predetermined device such as the noise radiation unit 14 or the like installed in the storage room r2 is connected to one of concentrated cables drawn out from the lower part of the gantry 6, via a filter panel provided in a double floor structure of the shield room R1 and the floor board 1b. The filter panel is a wiring panel having electromagnetic shielding properties and is installed, for example, on the floor board 1b or in the storage room r2, and not shown in FIGS. 1A and 1C. Cables drawn out from predetermined devices such as the noise radiation unit 14 installed in the storage room r2 or the cables drawn out from the gantry 6 are concentrated to the unit U1 or the like installed in the machine room R2 via the filter panel 200 provided on the wall between the storage room r2 and the machine room R2.

With this structure, the cables connecting between the units arranged in different spaces can be concentrated in one place with the electromagnetic shielding property maintained. As a result, the work burden for installation, maintenance, inspection, etc., can be reduced.

(Structure for Maintenance/Inspection of Units to be Located in Storage Room r2)

In the case of maintenance or repair of the noise radiation unit 14 such as the control unit 2 arranged in the storage room r2, it is required to detach a part of the board portion 100 and confirm the wiring and inside of each unit from the imaging room r1 side. To meet this requirement, the noise radiation unit 14 and the like, which the magnetic resonance imaging apparatus 1a according to the present embodiment comprises and is also installed in the storage room r2, has an opening and the like. The opening and the like allow a user to access (for maintenance and inspection) the various switches provided at upper surface of the noise radiation unit 14, connection terminals, display screen, pilot lamp, and a device provided inside of the noise radiation unit 14. According to this structure, the user can easily inspect the wiring and the inside of each unit from the imaging room r1 side. As a result, the burden of work at the time of maintenance and inspection can be greatly reduced.

(First Modification)

Figure 3:
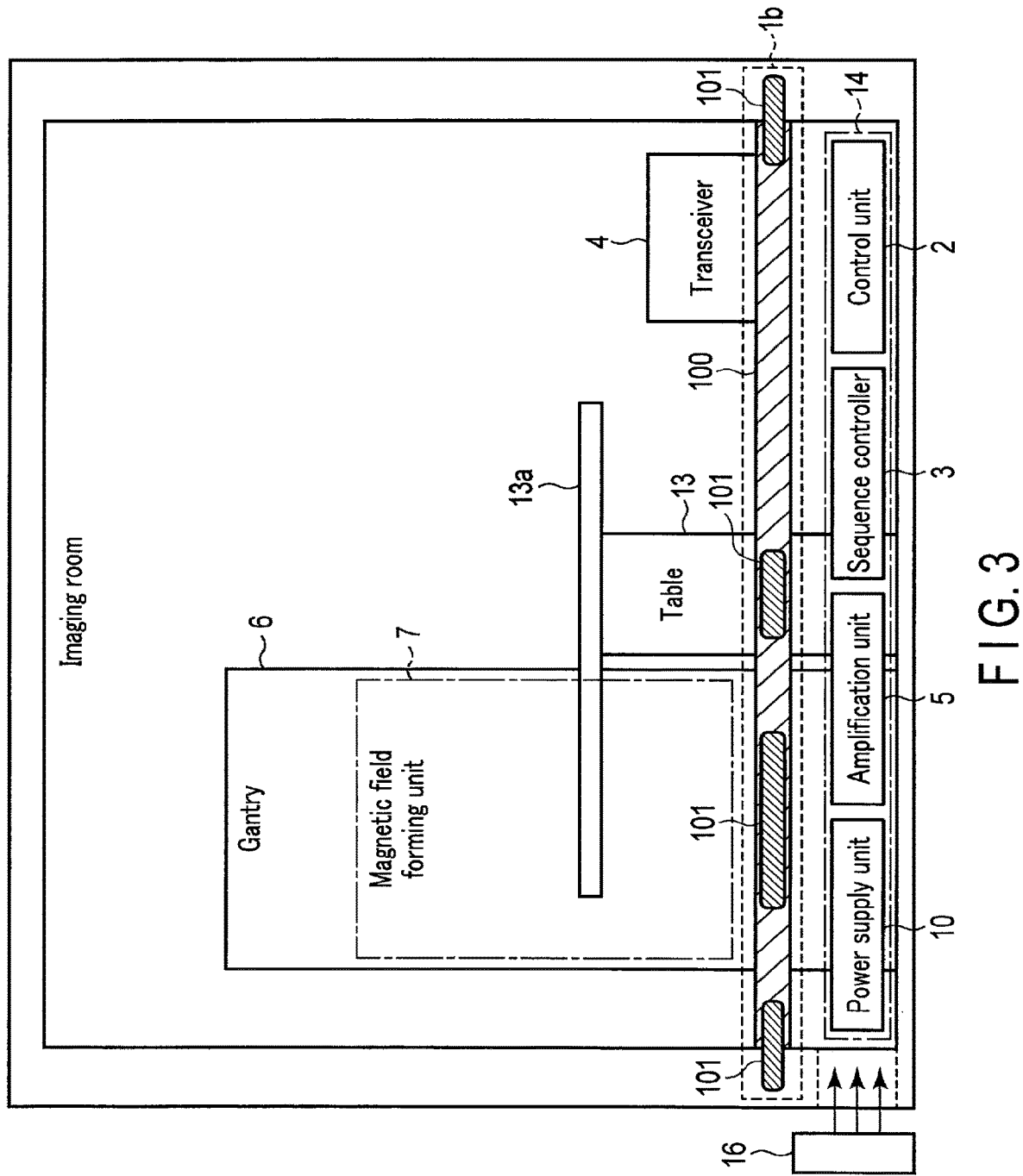
FIG. 3 is a plan view showing a modified example of the magnetic resonance imaging system according to the first embodiment comprising a cooling fan and the magnetic resonance imaging apparatus.

FIG. 3 is a plan view showing a modification including a cooling fan 16 (cooling mechanism) in the magnetic resonance imaging apparatus 1a according to the first embodiment. In this modification, a vent hole is provided at part of the wall between the storage room r2 and the outside of the storage room r2 (for example, the machine room R2). Additionally, the cooling fan 16 is installed near the vent hole outside of the storage room r2. The cooling fan 16 generates convection in the second space, thereby cooling, for example, the power supply unit 10 that generates heat. The cooling fan 16 does not operate in a magnetic field environment because it uses a motor. For this reason, in the modification, the cooling fan 16 is installed outside of the storage room r2 for safety's sake. However, if the magnetic shielding performance of the board portion 100 of the floor board 1b is improved, the cooling fan 16 may be installed in the storage room r2, like the noise radiation unit 14.

(Second Modification)

Figure 4A:
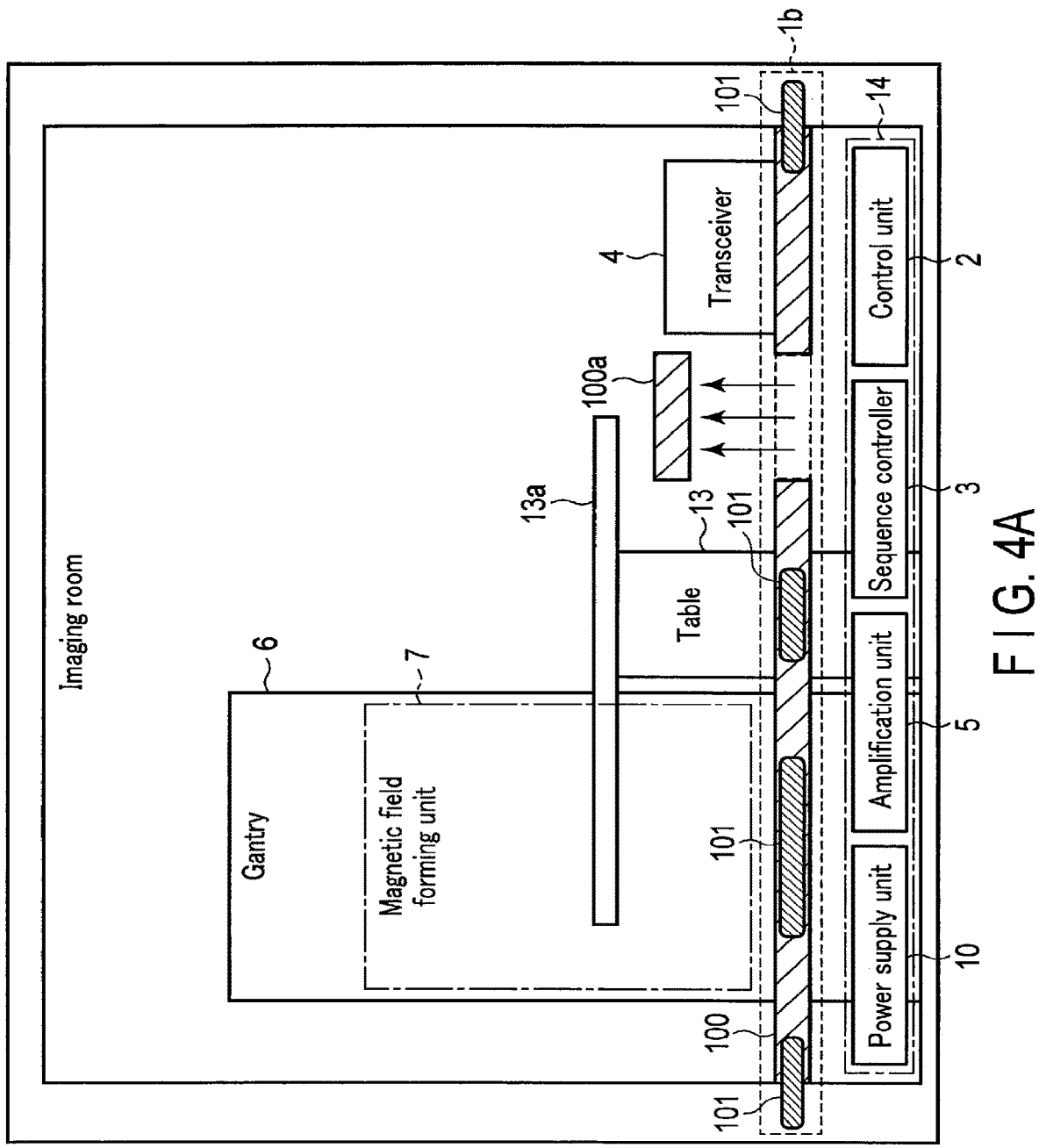
FIG. 4A is a plan view showing a modified example including a floorboard that can be partially detached in the magnetic resonance imaging system according to the first embodiment comprising the magnetic resonance imaging apparatus.

FIG. 4A is a plan view showing a modification including a partially detachable floor board 1b in the magnetic resonance imaging apparatus 1a according to the first embodiment. In this modification, the board portion 100 of the floor board 1b includes a detachable hatch 100a. In FIG. 4A, one detachable hatch 100a is shown, but in reality, a plurality of detachable hatches 100a may be used. Further, in the case where the board portion 100 is constituted by a plurality of assembled panels, the detachable hatch 100a may be realized by one or several detachable panels.

For example, when doing inspection and maintenance, or the like of the noise radiation unit 14, a user such as a service person or a doctor detaches the detachable hatch 100a from the board portion 100 for the purpose of doing inspection or maintenance of the control unit 2, the sequence controller 3, and the like. After the inspection or maintenance has been done, the service person or the like attaches the detachable hatch 100a to the board portion 100 again. In this way, by detaching the detachable hatch 100a, the unit installed in the storage room r2 can be quickly and easily accessed.

(Modification 3)

In FIGS. 1A and 1C, some cases are exemplified in which a plurality of units arranged in the storage room r2 are connected to each other by cables, and performs communication and the like. The technical concepts of the present embodiment are not being limited to this example. A plurality of units arranged in the storage room r2 may perform wireless communication with each other as shown in FIG. 4B. Likewise, a plurality of units arranged in the storage room r2 and a predetermined unit installed in the machine room R2 may perform wireless communication with each other. In addition, wireless communication and wired communication may be used in combination depending on the installation environment. As shown in FIG. 4B, the antenna for wireless communication provided on the side of a predetermined unit installed in the machine room R2 is provided in the storage room r2 via the filter panel 200.

(Installation Method)

Figure 5:
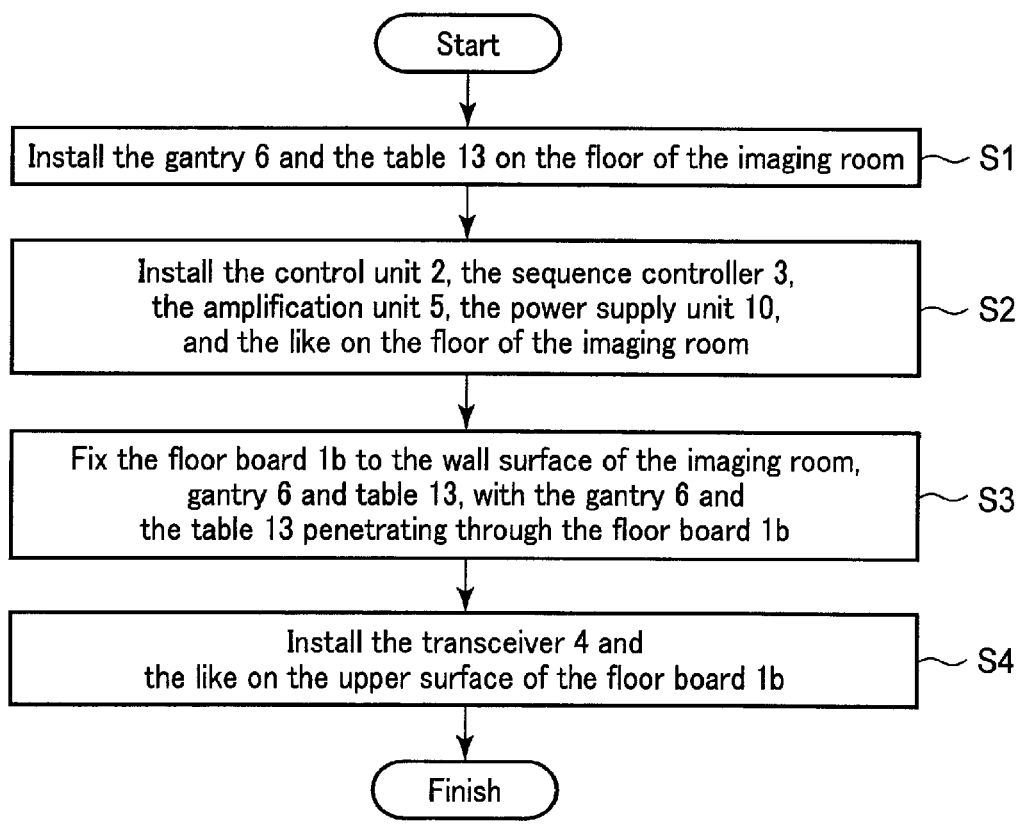
FIG. 5 is a flowchart showing an example of a method of installing a magnetic resonance imaging system according to the first embodiment comprising the magnetic resonance imaging apparatus.

FIG. 5 is a flowchart showing an example of a method of installing the magnetic resonance imaging apparatus 1a according to the first embodiment.

(Step S1)

In step S1, the gantry 6 and the table 13 are placed on the surface of the floor of the shield room R1. Note that the internal structure of the gantry 6 including the magnetic field forming unit 7 and the like is assumed to be normally completed at the installation stage.

(Step S2)

In step S2, the noise radiation unit 14 including the control unit 2, the sequence controller 3, the amplification unit 5, and the power supply unit 10 is placed on the surface of the floor of the shield room R1.

(Step S3)

In step S3, the floor board 1b is fixed to the wall surface of the shield room R1, the gantry 6 and the table 13 so that the gantry 6 and the table 13 penetrate through the floor board 1b via the board fixing jig 101. Note that the floor board 1b needs to be shaped in advance in conformity with the gantry 6, the table 13, and the shape of the wall surface of the shield room R1. Alternatively, the shape of the floor board 1b may be processed in this step.

Magnetic shielding processing and high-frequency noise insulation processing of the floor board 1b are usually preferable to be performed in advance, however, in this step, these processing may be performed.

( Step S4)

In step S4, for example, some units such as the transceiver 4 which should be placed near the magnetic field forming unit because of structural requirement are placed on the upper surface of the floor board 1b.

(When Using Modification)

When using the cooling fan 16 according to the first modification and installing it outside the shield room R1 (for example, the machine room R2), the cooling fan 16 can be installed in any step or may be installed in advance. When using the partially detachable floor board 1b according to the second modification, the above-described various units placed on the surface of the floor of the shield room R1 in step S2 may be placed after step S3, for example, before or after step S4 or in the same step as step S4.

Although not illustrated in the steps of the installation method, wiring for wired communication, power supplies, and the like are installed appropriately in each step.

(Effects)

According to the magnetic resonance imaging apparatus 1a of the first embodiment, the following effects can be obtained.

The board portion 100 of the floor board 1b undergoes magnetic shielding processing and high-frequency noise insulation processing. The floor board 1b is located above the control unit 2, the sequence controller 3, the amplification unit 5, and the power supply unit 10 and under the magnetic field forming unit 7 of the gantry 6. The floor board 1b is located to spatially divide the noise radiation unit 14 and the magnetic field forming unit 7. This can prevent operation errors and device fatigue caused by the influence of a magnetic field on various units such as the control unit 2, the sequence controller 3, the amplification unit 5, and the power supply unit 10. Since the RF reception coil 9c is not affected (or hardly affected) by high-frequency noise (having a frequency close to the RF used to obtain NMR) radiated from the noise radiation unit 14, an MRI image of a higher resolution is expected to be generated. Also the design constraint in the magnetic shielding design for each of the various units can be relaxed. Similarly, the design constraint in the high-frequency noise insulation design for each of the various units can be relaxed. Due to the two relaxations of the constraints described above, the expandability of the magnetic resonance imaging apparatus 1a according to the first embodiment is improved. In addition, due to the two relaxations of the constraints described above, the cost of design can be reduced. In addition, for example, wireless communication can be implemented among the various units placed in the second space without any influence on a generated image. When a frequency (for example, infrared communication or the like) other than the RF band is used, wireless communication can be implemented between a unit placed in the first space and a unit placed in the second space. It is also possible to ensure the space for clearance in the imaging room r1 without vertical placement (not preferable from the viewpoint of device fatigue or the like) that is often done for the various units in a conventional imaging room.

In the first modification, a vent hole is provided in part of the wall between the shield room R1 and the outside of the shield room R1.

The cooling fan 16 is installed near the vent hole outside the shield room R1. Space saving can thus be implemented without requiring a large heat sink, a water cooling device, complex ducts, and the like which are needed when installing the various units in the shield room R1.

In the second modification, the board portion 100 of the floor board 1b includes the detachable hatch 100a. That is, the service person or the like can detach the detachable hatch 100a from the board portion 100 and attach the detachable hatch 100a to the board portion 100 again. Inspection, maintenance, or exchange of various units, in which workability is poor because the gantry cover needs to be detached, can be implemented by detaching the detachable hatch 100a, and the workability is expected to improve. It is also possible to realize the magnetic resonance imaging apparatus 1a that has not only higher workability for inspection, maintenance, or exchange of various units but also higher expandability than before for, for example, introduction of a new unit. At the time of expansion as well, a new unit can be arranged without losing the design quality of the gantry cover or the like.

(Second Embodiment)

Figure 6A:
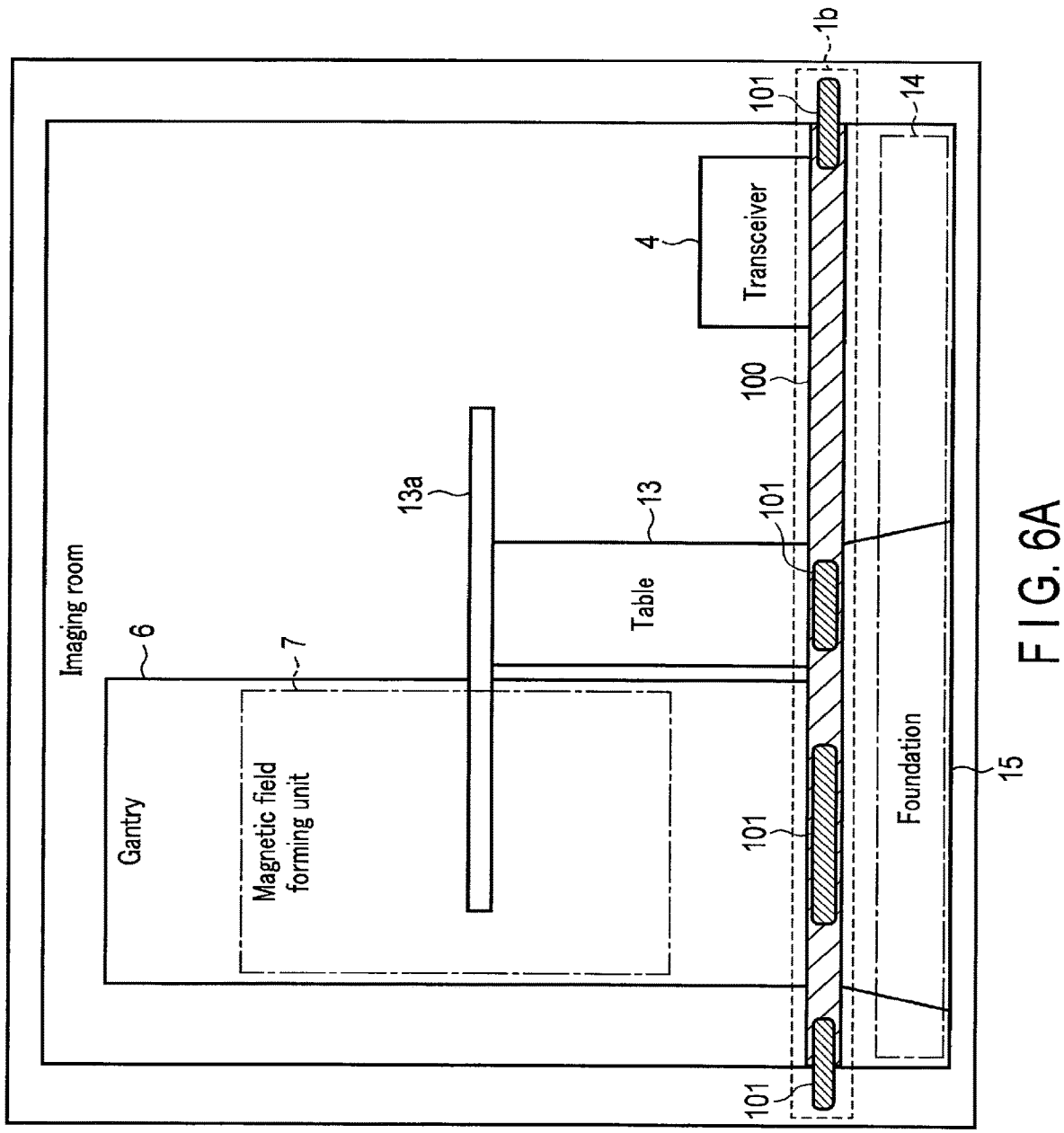
FIG. 6A is a plan view showing an example of a magnetic resonance imaging system according to the second embodiment comprising the magnetic resonance imaging apparatus.
Figure 6B:
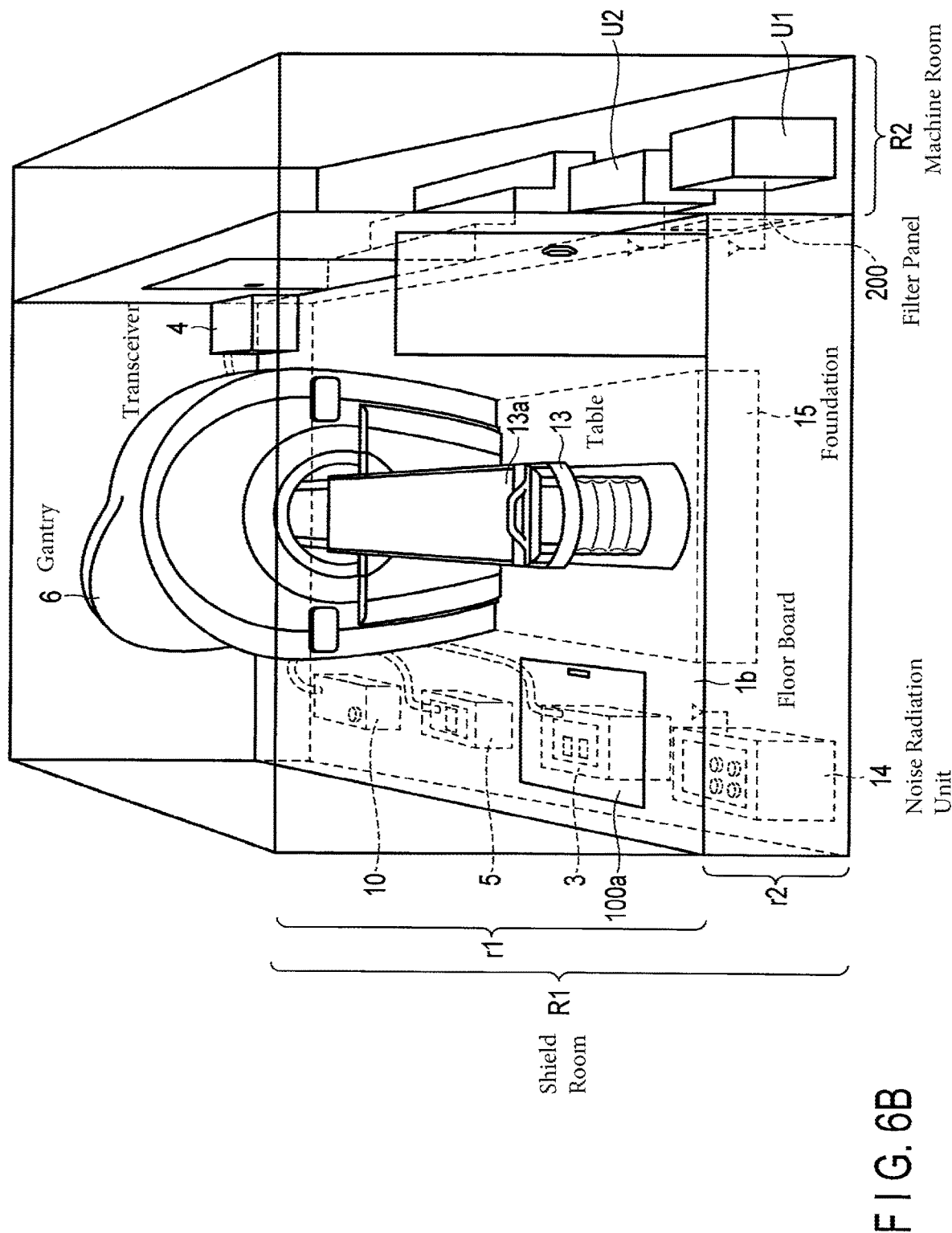
FIG. 6B is a bird's-eye view showing a magnetic resonance imaging apparatus according to the second embodiment and a shield room in which the magnetic resonance imaging apparatus is installed.

FIG. 6A is a plan view showing a magnetic resonance imaging apparatus 1a and the shield room R1 and the like where the magnetic resonance imaging apparatus is installed according to the second embodiment. FIG. 6B is a bird's-eye view showing an example of an installation form of the magnetic resonance imaging apparatus 1a according to the second embodiment. Note that a description of the same portions as in the magnetic resonance imaging apparatus 1a according to the first embodiment will be omitted.

In the magnetic resonance imaging apparatus 1a according to the second embodiment, a gantry 6 and the table 13 are placed on a floor board 1b, unlike the magnetic resonance imaging apparatus 1a according to the first embodiment. The masses of the gantry 6 and the table 13 are large. In particular, a magnetic field forming unit 7 in the gantry 6 has a large mass because it includes a static field magnet and the like. The foundation 15 which is durable to weight based on the mass of the gantry 6 is positioned vertically downward of the gantry 6 (and the table 13) so that the floor board 1b can withstand the weight based on the mass of the gantry 6, the floor board 1b is supported, and is placed on the floor surface of the shield room R1.

Since the gantry 6 is located on the floor board 1b, electromagnetic insulation between the first space and the second space is achieved at a higher accuracy in the magnetic resonance imaging apparatus 1a according to the second embodiment than in the magnetic resonance imaging apparatus 1a according to the first embodiment.

The first modification (use of a cooling fan 16) or the second modification (partially detachable floor board) described concerning the magnetic resonance imaging apparatus 1a according to the first embodiment may be implemented in the magnetic resonance imaging apparatus 1a according to the second embodiment.

(Installation Method)

Figure 7:
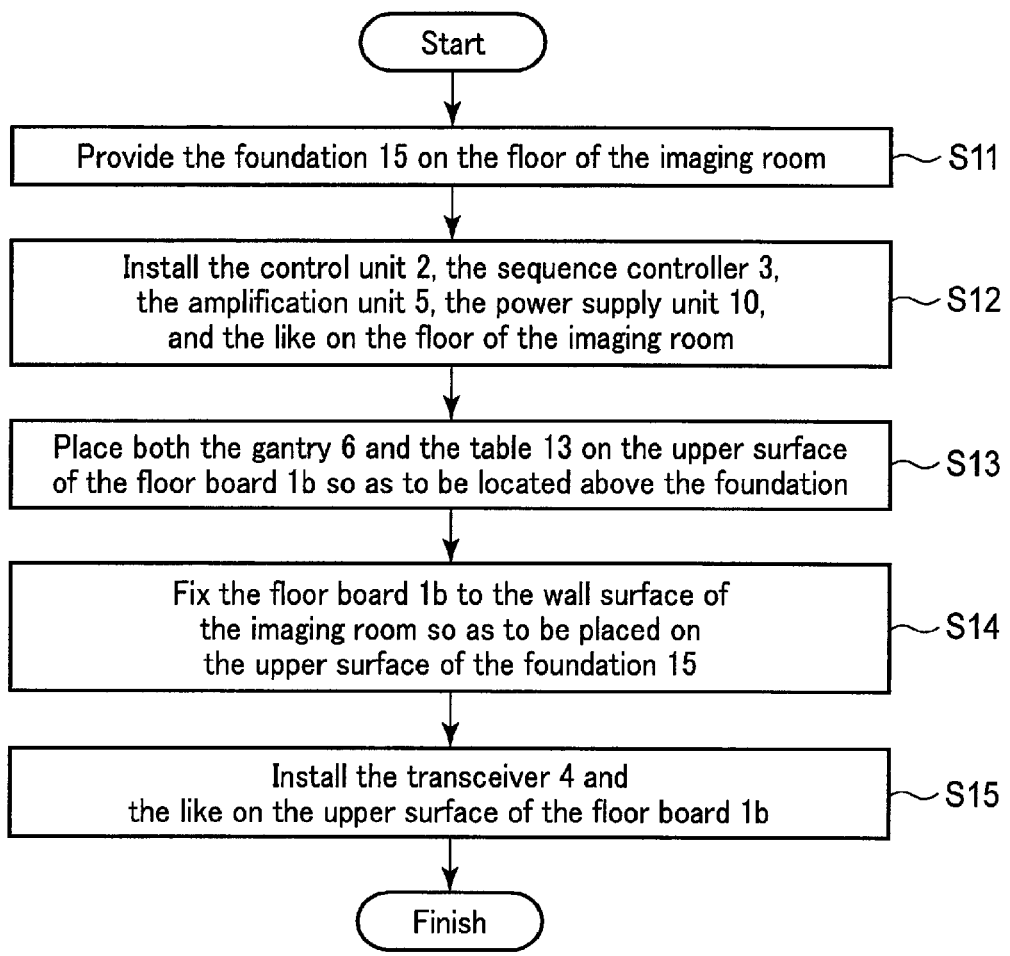
FIG. 7 is a flowchart showing an example of a method of installing a magnetic resonance imaging system according to the second embodiment comprising the magnetic resonance imaging apparatus.

FIG. 7 is a flowchart showing an example of a method of installing the magnetic resonance imaging apparatus 1a according to the second embodiment.

(Step S11)

In step S11, the foundation 15 capable of withstanding the weight based on the mass of the gantry 6 is provided on the surface of the floor of the shield room R1.

(Step S12)

In step S12, a noise radiation unit 14 including a control unit 2, a sequence controller 3, an amplification unit 5, and a power supply unit 10, etc. is placed on the surface of the floor of the shield room R1.

(Step S13)

In step S13, the floor board 1b is fixed to the wall surface of the shield room R1 via a board fixing jig 101. Note that the floor board 1b needs to be shaped in advance in conformity with the shape of the wall surface of the shield room R1. Alternatively, the floor board 1b may be shaped in this step.

Magnetic shielding processing and high-frequency noise insulation processing of the floor board 1b are usually preferable to be performed in advance, however, in this step, these processing may be performed.

(Step S14)

In step S14, the gantry 6 and the table 13 which have large masses are placed on the upper surface of the floor board 1b so as to be located above the foundation 15 in the vertical direction.

(Step S15)

In step S15, for example, some units such as the transceiver 4 which should be placed near the magnetic field forming unit because of structural requirement are placed on the upper surface of the floor board 1b.

(When Using Modification)

When using a cooling fan 16 according to the first modification and installing it outside the shield room R1 (for example, machine room R2), the cooling fan 16 can be installed in any step or may be installed in advance. When using the partially detachable floor board 1*b* according to the second modification, the above-described various units placed on the surface of the floor of the shield room R1 in step S12 may be placed after step S13, for example, before or after step S15 or in the same step as step S15.

Although not illustrated in the steps of the installation method, wiring for wired communication, power supplies, and the like are installed appropriately in each step.

(Effects)

According to the magnetic resonance imaging apparatus 1*a* of the second embodiment, the following effects can be obtained in addition to the effects of the magnetic resonance imaging apparatus 1*a* according to the above-described first embodiment.

In the magnetic resonance imaging apparatus 1*a* according to the second embodiment, the foundation 15 which is durable to weight based on the mass of the gantry 6 is positioned vertically downward of the gantry 6 (and the table 13) so that the floor board 1*b* can withstand the weight based on the mass of the gantry 6, the floor board 1*b* is supported, and is placed on the floor surface of the shield room R1. Hence, the floor board 1*b* can easily be shaped as compared to the magnetic resonance imaging apparatus 1*a* according to the first embodiment.

In the magnetic resonance imaging apparatus 1*a* according to the first embodiment, the floor board 1*b* is arranged with a height to some extent relative to the surface of the floor of the shield room R1. For this reason, the height of the tabletop 13*a* or the subject placement space in the gantry 6 is less than the height in a conventional magnetic resonance imaging apparatus. On the other hand, in the magnetic resonance imaging apparatus 1*a* according to the second embodiment, it is possible to obtain the same effects as in the magnetic resonance imaging apparatus 1*a* according to the above-described first embodiment while maintaining the same height of the tabletop 13*a* or the subject placement space in the gantry 6 of the conventional magnetic resonance imaging apparatus.

Since the gantry 6 is located on the floor board 1*b*, electromagnetic insulation between the first space and the second space is achieved at a higher accuracy in the magnetic resonance imaging apparatus 1*a* according to the second embodiment than in the magnetic resonance imaging apparatus 1*a* according to the first embodiment. This can prevent device fatigue of various units placed in the second space and implement generation of an MRI image with less noise.

Note that the present invention is not exactly limited to the above embodiments, and constituent elements can be modified in the stage of practice without departing from the spirit and scope of the invention. Various inventions can be formed by properly combining a plurality of constituent elements disclosed in the above embodiments. For example, several constituent elements may be omitted from all the constituent elements described in the embodiments. In addition, constituent elements throughout different embodiments may be properly combined.

What is claimed is:

1. A magnetic resonance imaging apparatus installed in a shield room comprising:
   a gantry including a static magnetic field magnet, a gradient magnetic field coil, and an RF coil;
   a table on which a subject is to be placed; and
   at least one unit related to control of the magnetic resonance imaging apparatus and including at least one opening on an upper surface thereof for maintenance and inspection, wherein
   the at least one unit is located between a floor of the shield room and a board which divides the shield room, the board being at a predetermined height from the floor, and
   the gantry and the table are installed on the floor and penetrate the board.

2. The apparatus according to claim 1, wherein the at least one unit includes at least one RF amplifier to amplify RF pulses supplied to the RF coil.

3. The apparatus according to claim 1, wherein a plurality of units is installed in a space between a floor surface of the shield room and said board and is configured to perform wireless communication with each other.

4. The apparatus according to claim 3, wherein the plurality of units include at least one RF amplifier to amplify RF pulses supplied to the RF coil.

5. The apparatus according to claim 3, at least one first unit is installed in the space between the floor surface of the shield room and the board, and
   at least one second unit is installed in a space outside of the shield room, wherein
   the at least one first unit and the at least one second unit perform wireless communication with each other.

6. The apparatus according to claim 5, the at least one first unit includes the RF amplifier to amplify RF pulses supplied to the RF coil.

7. The apparatus according to claim 1, wherein the table does not include a vertical movement mechanism.

8. A method for installing a magnetic resonance imaging apparatus in a shield room comprising:
   installing a gantry including a static magnetic field magnet, a gradient magnetic field coil and an RF coil, and a table placed on a floor surface of the shield room;
   forming a double floor structure by constructing a board at a position of a predetermined height from the floor surface of the shield room; and
   installing at least one unit of the magnetic resonance imaging apparatus in a space between the floor surface of the shield room and the board which divides the shield room, the board being at the predetermined height from the floor surface, wherein
   the gantry and the table are installed on the floor surface and penetrate the board.

9. The method according to claim 8, wherein the board includes electromagnetic shielding function.

10. The method according to claim 8, wherein the at least one unit installed in the space between the floor surface of the shield room and the board is at least one RF amplifier to amplify RF pulses supplied to the RF coil.

11. The method according to claim 8, wherein the at least one unit installed in the space between the floor surface of the shield room and the board is connected to at least one of concentrated cables drawn out from a lower part of the gantry via a filter panel provided in the double floor structure.

12. The method according to claim 8, wherein at least a part of the board is removable.

13. A method for installing a magnetic resonance imaging apparatus in a shield room comprising:
   installing a gantry including a static magnetic field magnet, a gradient magnetic field coil and an RF coil, and a table placed on a foundation provided a floor surface of on the shield room;
   forming a double floor structure by constructing a board at a position of a predetermined height from the floor surface of the shield room; and installing at least one unit of the magnetic resonance imaging apparatus in a space between the floor surface of the shield room and the board which divides the shield room, the board being at the predetermined height from the floor surface, wherein the gantry and the table are installed on the foundation and penetrate the board.

14. The method according to claim 13, wherein the board includes electromagnetic shielding function.

15. The method according to claim 13, wherein the at least one unit installed in the space between the floor surface of the shield room and the board is at least one RF amplifier to amplify RF pulses supplied to the RF coil.

16. The method according to claim 13, wherein the at least one unit installed in the space between the floor surface of the shield room and the board is connected to at least one of concentrated cables drawn out from a lower part of the gantry via a filter panel provided in the double floor structure.

17. The method according to claim 13, wherein at least a part of the board is removable.

* * * * *